United States Patent [19]

Oxford

[11] Patent Number: 5,037,845

[45] Date of Patent: Aug. 6, 1991

[54] INDOLE DERIVATIVE

[75] Inventor: Alexander W. Oxford, Royston, England

[73] Assignee: Glaxo Group Limited, England

[21] Appl. No.: 317,682

[22] Filed: Mar. 1, 1989

Related U.S. Application Data

[63] Continuation of Ser. No. 82,666, Aug. 7, 1987, abandoned, which is a continuation of Ser. No. 761,392, Aug. 1, 1985, abandoned.

[30] Foreign Application Priority Data

Aug. 1, 1984 [GB] United Kingdom ............... 8419575

[51] Int. Cl.[5] ................... A61K 31/40; C07D 209/16
[52] U.S. Cl. ..................................... 514/415; 548/504
[58] Field of Search ...................... 548/504; 514/415

[56] References Cited

U.S. PATENT DOCUMENTS

| 3,322,787 | 5/1967 | Sletzinger et al. | 548/500 |
|---|---|---|---|
| 3,624,103 | 11/1971 | De Martiis et al. | 548/500 |
| 4,283,410 | 8/1981 | Schut et al. | 548/500 |
| 4,816,470 | 3/1989 | Dowle et al. | 514/415 |

FOREIGN PATENT DOCUMENTS

| 145459 | 6/1985 | European Pat. Off. |
| 8115513 | 2/1982 | France |
| 8115514 | 2/1982 | France |
| 8115515 | 2/1982 | France |
| 8309429 | 1/1984 | France |
| 8418618 | 6/1985 | France |

OTHER PUBLICATIONS

M. Dorole et al., Chem. Abst., vol. 100, No. 103175y (1983).

*Primary Examiner*—Mary E. Ceperley
*Attorney, Agent, or Firm*—Bacon & Thomas

[57] ABSTRACT

A compound of formula (I)

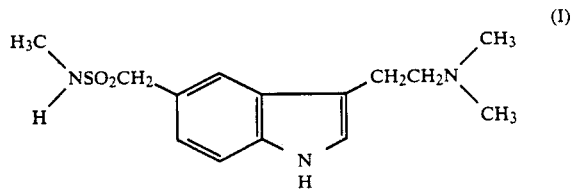

and its physiologically acceptable salts and solvates are described as useful in treating and/or preventing pain resulting from dilatation of the cranial vasculature in particular migraine.

The compound (I) may be prepared, for example, by cyclizing a compound of formula (II)

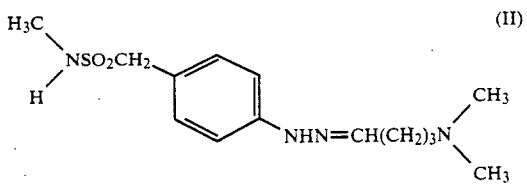

12 Claims, No Drawings

INDOLE DERIVATIVE

This application is a continuation, of application Ser. No. 082,666, filed Aug. 7, 1987 now abandoned, which is a continuation of Ser. No. 761,392, filed Aug. 1, 1985, which is now abandoned.

This invention relates to an indole derivative of use in the treatment of migraine, to processes for its preparation, to pharmaceutical compositions containing it and to its medical use.

The pain of migraine is associated with excessive dilatation of the cranial vasculature and known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache, and a compound having a selective vasoconstrictor activity would fulfil such a role.

Furthermore, in conditions such as migraine, where the drug will usually be administered by the patient, it is highly desirable that the drug can be taken orally. It should therefore possess good bioavailability and be effectively absorbed from the gastro-intestinal tract so that prompt relief of symptoms can occur. The drug should also be safe (i.e. free from toxic effects) when administered by the oral route.

A wide variety of indole derivatives have been described as being of use in the treatment of migraine. In our published UK Patent Application No. 2124210A we describe indoles of the general formula

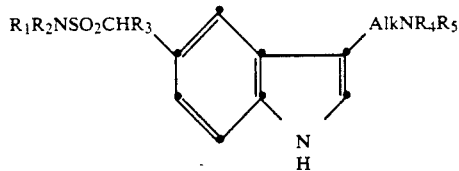

wherein $R_1$ represents a hydrogen atom or a $C_{1-6}$ alkyl or $C_{3-6}$ alkenyl group; $R_2$ represents a hydrogen atom or a $C_{1-3}$ alkyl, $C_{3-6}$ alkenyl, aryl, ar($C_{1-4}$)alkyl or $C_{5-7}$ cycloalkyl group; $R_3$ represents a hydrogen atom or a $C_{1-3}$ alkyl group; $R_4$ and $R_5$, which may be the same or different, each represents a hydrogen atom or a $C_{1-3}$ alkyl or propenyl group or $R_4$ and $R_5$ together form an aralkylidene group; and Alk represents an alkylene chain containing two or three carbon atoms which may be unsubstituted or substituted by not more than two $C_{1-3}$ alkyl groups, and physiologically acceptable salts and solvates thereof.

As indicated in UK Patent Application No. 2124210A, compounds of the above formula selectively constrict the carotid arterial bed of the anaesthetised dog and are thus potentially useful for the treatment of migraine.

We have now found a particular compound which falls within the scope of the group of compounds described and claimed in UK Patent Application No. 2124210A but which is not specifically disclosed therein, which compound has special advantages. Thus, we have discovered that by a selection of two specific substituents, namely the methylaminosulphonylmethyl group at the 5-position of the indole nucleus and the N,N-dimethylaminoethyl substituent at the 3-position, a compound having a combination of highly advantageous properties for the treatment of migraine is obtained.

Thus the present invention provides 3-[2-(dimethylamino)ethyl]-N-methyl-1H-indole-5-methanesulphonamide, of formula (I)

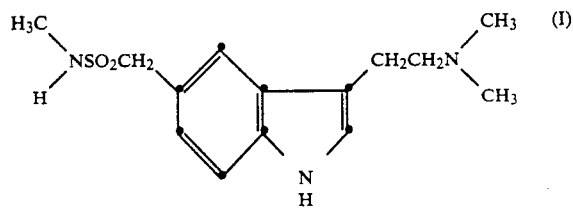

and its physiologically acceptable salts and solvates (e.g. hydrates).

The compounds according to the invention are useful in treating and/or preventing pain resulting from dilatation of the cranial vasculature, in particular migraine and related disorders such as cluster headache.

The compound of formula (I) potently and selectively constricts the carotid arterial bed following intravenous administration as shown by tests in anaesthetised dogs. This potent and selective vasoconstrictor action has also been demonstrated in vitro. Further tests in anaesthetised dogs have shown that the compound of formula (I) is effectively and consistently well absorbed from the gastro-intestinal tract following intra-duodenal administration, quickly producing a sustained vasoconstriction in the carotid arterial bed.

At doses at which the compound of formula (I) would be efficacious in the treatment of migraine it has no significant effect on blood pressure and heart rate and no significant bronchoconstrictor effect on the lung.

The compound of formula (I) may safely be administered orally as well as intravenously.

The combination of these properties possessed by the compound of formula (I) is highly desirable in the treatment of migraine and the compound (I) has significant advantages, as demonstrated by the aforementioned experimental tests, over compounds which have previously been described as being of use in the treatment of migraine, such as those disclosed in published UK Patent Application No. 2124210A. It is particularly advantageous that the compound of formula (I) is effectively absorbed from the gastro-intestinal tract in a consistent manner.

Furthermore, tests in guinea pigs have shown that the compound of formula (I) promotes gastric emptying following oral administration, and hence relieves gastric stasis. Gastric stasis is a symptom commonly associated with migraine. Hence the ability of the compound of formula (I) to relieve gastric stasis is a further beneficial property of this compound in the treatment of migraine.

Suitable physiologically acceptable salts of the compound of formula (I) include acid addition salts formed with organic or inorganic acids for example hydrochlorides, hydrobromides, sulphates, nitrates, phosphates, formates, mesylates, citrates, benzoates, fumarates, maleates and succinates. Other salts may be useful in the preparation of the compound of formula (I) e.g. creatinine sulphate adducts, and salts with e.g. toluene-p-sulphonic acid.

Where a salt of the compound (I) according to the invention is formed with a dicarboxylic acid, such as succinic acid, the salt may be formed with either one or both of the carboxylic acid groups, i.e. the salt may contain either one or two moles of the compound (I) per mole of acid. A preferred salt according to the invention is the succinate, most preferably the 1:1 succinate.

According to a further aspect, the invention provides a method of treatment of a human subject suffering from or susceptible to pain resulting from dilatation of the cranial vasculature, such as migraine or cluster headache, by administration of a compound of formula (I) or a physiologically acceptable salt or solvate thereof. The method of treatment preferably comprises oral administration of a compound of the invention.

Accordingly, the invention also provides a pharmaceutical composition adapted for use in medicine which comprises the compound of formula (I) and/or a physiologically acceptable salt or solvate (e.g. hydrate) thereof, formulated for administration by any convenient route. Such compositions may be formulated in conventional manner using one or more pharmaceutically acceptable carriers or excipients. The compounds according to the invention may be formulated for oral, sub-lingual, parenteral, rectal or intra-nasal administration, or in a form suitable for administration by inhalation or insufflation. Formulations of the compounds for oral administration are preferred.

The pharmaceutical compositions for oral administration may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, sucrose, mannitol, maize starch, microcrystalline cellulose or calcium hydrogen phosphate); lubricants (e.g. stearic acid, polyethylene glycol, magnesium stearate, talc or silica); disintegrants (e.g.) potato starch, sodium starch glycollate or croscarmellose sodium); or wetting agents (e.g. sodium lauryl sulphate). The tablets may be coated by methods well known in the art. Liquid preparations for oral administration may take the form of, for example, aqueous or oily solutions, syrups, elixirs, emulsions or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives, glucose/sugar syrup, gelatin, aluminum stearate gel, or hydrogenated edible fats); emulsifying agents (e.g. lecithin, acacia or sorbitan mono-oleate); non-aqueous vehicles (e.g. almond oil, oily esters, ethyl alcohol or fractionated vegetable oils); and preservatives (e.g. methyl or propyl p-hydroxybenzoates or sorbic acid). The liquid preparations may also contain conventional buffers, flavouring, colouring and sweetening agents as appropriate.

A proposed dose of the compounds of the invention for oral administration to man (about 70 kg bodyweight) for the treatment of migraine is 0.1 mg to 100 mg, for example 0.5 mg to 50 mg; preferably 2 mg to 40 mg, of the active ingredient per dose which could be administered up to 8 times per day, more usually 1 to 4 times per day. It will be appreciated that it may be necessary to make routine variations to the dosage depending on the age and weight of the patient, as well as the severity of the condition to be treated. It should be understood that unless otherwise indicated, the dosages are referred to in terms of the weight of compound (I) as the free base.

The compounds of the invention may be formulated for parenteral administration by injection, preferably intravenous or subcutaneous injection e.g. by bolus injection or continuous intravenous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents and/or agents to adjust the tonicity of the solution. Alternatively, the active ingredient may be in powder form for constitution with a suitable vehicle, e.g. sterile pyrogen-free water, before use.

The overall daily dose administered by injection may be in the range 50 $\mu$g to 50 mg, e.g. 0.5 to 20 mg, which may for example be divided into 2,3 or 4 doses.

The compounds of the invention may also be formulated in rectal compositions such as suppositories or retention enemas, e.g. containing conventional suppository bases such as cocoa butter or other glycerides.

Tablets for sub-lingual administration may be formulated in a similar manner to those for oral administration.

For intra-nasal administration the compounds of the invention may be used as a liquid spray or in the form of drops.

Dosages of the compounds of the invention for rectal, sublingual or intranasal administration to man (of average body weight e.g. about 70 kg) for the treatment of migraine may be similar to those described previously for oral administration.

For administration by inhalation the compounds according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Aerosol formulations are preferably arranged so that each metered dose or "puff" delivered from a pressurized aerosol contains 0.2 mg to 2 mg of a compound of the invention, and each dose administered via capsules and cartridges in an insufflator or an inhaler contains 0.2 mg to 20 mg of a compound of the invention. Administration may be several times daily, for example from 2 to 8 times, giving for example 1, 2 or 3 doses each time. The overall daily dose by inhalation will be similar to that for oral administration.

The compounds of the invention may, if desired, be administered in combination with one or more other therapeutic agents, such as analgesics, anti-inflammatory agents and anti-nauseants.

The compound of formula (I) and its physiologically acceptable salts and solvates (e.g. hydrates) may be prepared by the general methods outlined hereinafter.

According to one general process (A), the compound of formula (I) may be prepared by cyclisation of the compound of formula (II)

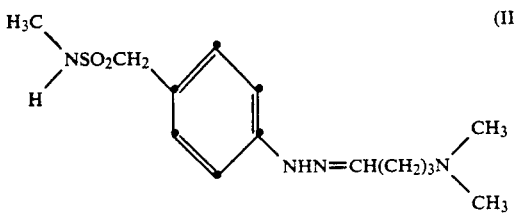

The reaction may conveniently be effected in aqueous or non-aqueous reaction media and at temperatures of from 10° to 200° C., preferably 50° to 125° C.

Particularly convenient embodiments of process (A) are described below.

The cyclisation is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in aqueous or non-aqueous media, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be for example an inorganic acid such as concentrated hydrochloric or sulphuric acid or an organic acid, such as acetic acid. (In some cases the acid catalyst may also act as the reaction solvent). In an anhydrous reaction medium, which may comprise one or more alcohols or ethers (e.g. as previously described) or esters (e.g. ethyl acetate), the acid catalyst will generally be a Lewis acid such as boron trifluoride, zinc chloride or magnesium chloride.

According to a particular embodiment of this cyclisation process, the compound of formula (I) may be prepared directly by the reaction of the compound of formula (III)

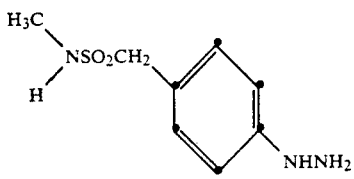

or a salt (e.g. the hydrochloride salt) thereof, with the compound of formula (IV)

or a salt or protected derivative thereof (such as an acetal, for example, a dialkyl or cyclic acetal e.g. formed with an appropriate alkyl orthoformate or diol, or protected as a bisulphite addition complex), using the appropriate conditions as previously described for the cyclisation of the compound of formula (II). (The Fischer-Indole Synthesis, B. Robinson p488-Wiley 1982). It will be appreciated that in this embodiment of the cyclisation process (A) a compound of formula (II) is formed as an intermediate and reacted in situ to form the desired compound of formula (I).

The compound of formula (II) may, if desired, be isolated as an intermediate by reacting the compound of formula (III), or a salt or protected derivative thereof with the compound of formula (IV) or a salt or protected derivative thereof, in water or in a suitable solvent, such as an aqueous alcohol (e.g. methanol) or an aqueous ether (e.g. dioxan) and at a temperature of, for example, from 10° to 30° C. If an acetal of the compound of formula (IV) is used it may be necessary to carry out the reaction in the presence of an organic or inorganic acid (for example, acetic or hydrochloric acid).

The compound of formula (III) may be prepared for example as described in UK Patent Application No. 2124210A.

As illustrated in the following general processes (B) and (C), the dimethylamino substituent may be introduced at the 3-position by conventional techniques involving modification of a substituent at the 3-position or direct introduction of the aminoalkyl substituent into the 3-position.

Thus a further general process (B) for preparing the compound of formula (I) involves reacting a compound of general formula (V)

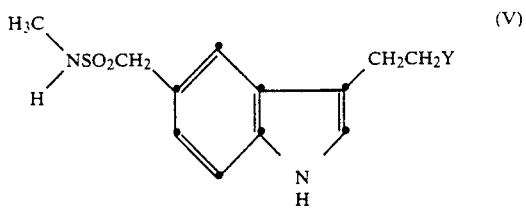

(wherein Y is a readily displaceable atom or group) or a protected derivative thereof, with dimethylamine.

Suitable displaceable atoms or groups Y include a halogen atom (e.g. chlorine, bromine or iodine); a group $OR_6$ where $OR_6$ is, for example, an acyloxy group, which may be derived from a carboxylic or sulphonic acid, such as an acetoxy, chloroacetoxy, dichloroacetoxy, trifluoroacetoxy, p-nitrobenzoyloxy p-toluenesulphonyloxy or methanesulphonyloxy group; or a group $\oplus NR_7R_8R_9 E^{\ominus}$, where $R_7$, $R_8$ and $R_9$ each represents a $C_{1-3}$ alkyl group, and $E^-$ represents an anion such as a halide ion, e.g. a chloride, bromide or iodide ion.

The displacement reaction may conveniently be effected in an inert organic solvent (optionally in the presence of water), examples of which include alcohols, e.g. ethanol; cyclic ethers e.g. dioxan or tetrahydrofuran; acyclic ethers, e.g. diethylether; esters e.g. ethyl acetate; amides e.g. N,N-dimethylformamide; and ketones e.g. acetone, methylethylketone or methylisobutylketone. The process may be carried out at a temperature of, for example, −10° to +150° C., preferably 20° to 100° C.

The compounds of formula (V) wherein Y is a halogen atom may be prepared by reacting the hydrazine of formula (III) with an aldehyde (or a protected derivative thereof) of formula (VI)

OHC(CH$_2$)$_3$Y  (VI)

(wherein Y is as previously defined) in an aqueous alcohol (e.g. methanol) or an aqueous ether (e.g. dioxan) containing an acid (e.g. acetic or hydrochloric acid) or by reacting the compound of formula (VII)

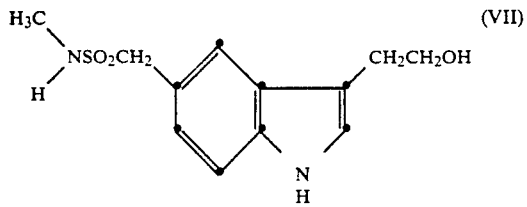

(VII)

with the appropriate halogenating agent such as a phosphorus trihalide, thionyl chloride or N-bromosuccinimide and triphenylphosphine, in a suitable solvent, for example pyridine or tetrahydrofuran. The compound of formula (VII) may also be used to prepare compounds of formula (V), wherein Y is a group OR$_6$ by acylation with the appropriate activated species derived from a carboxylic or sulphonic acid (e.g. an anhydride or sulphonyl chloride) using conventional techniques. The alcohol (VII) may be prepared for example by cyclisation of the appropriate hydrazone as described in UK Published Patent Application No. 2150932A.

Compounds of formula (V) where Y represents the group $\oplus$NR$_7$R$_8$R$_9$E$\ominus$ may be prepared from the corresponding primary amine by reaction with an appropriate alkylating agent, for example as described in general process (E) hereinafter.

The compound of formula (I) may also be prepared by another general process (C) involving reduction of a compound of general formula (VIII)

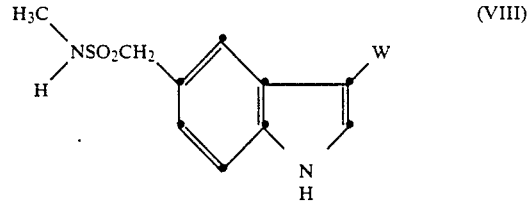

(VIII)

(wherein W is a group capable of being reduced to give the required dimethylaminoethyl group) or a salt or protected derivative thereof.

The required —(CH$_2$)—$_2$ and dimethylamino moieties may be formed by reduction steps which take place separately or together in any appropriate manner.

Groups which may be reduced to the —(CH$_2$)—$_2$ moiety include the corresponding unsaturated group and corresponding groups containing one or more carbonyl functions and/or a hydroxyl group.

The group W may be a group which is itself reduced to the dimethylaminoethyl moiety. Examples of such groups include —(CH$_2$)$_2$N(CH$_3$)COR$_{10}$ (where R$_{10}$ represents a hydrogen atom, or an alkoxy or aralkoxy group); —COCON(CH$_3$)$_2$; —CH$_2$CON(CH$_3$)$_2$; —CH(OH)CH$_2$N(CH$_3$)$_2$; and —COCH$_2$N(CH$_3$)$_2$.

Alternatively W may represent a group which gives the dimethylaminoethyl moiety upon reduction in the presence of dimethylamine, for example —CH$_2$CN and —CH$_2$CHO.

A particularly suitable method for preparing the compound of formula (I) is reductive methylation of the corresponding amino or methylamino derivative with formaldehyde in the presence of a suitable reducing agent. It will be appreciated that at least two equivalents of formaldehyde should be used when the starting material is the primary amine. If desired, the formaldehyde may first be condensed with the amine and the intermediate thus formed may subsequently be reduced.

Reduction of the compound of formula (VIII) may be effected by conventional methods, for example by catalytic hydrogenation or using a reducing agent such as an alkali metal or alkaline earth metal borohydride or cyanoborohydride. The reduction may conveniently be effected in an organic reaction medium which may comprise one or more organic solvents. Suitable solvents include alcohols, e.g. ethanol or propanol; cyclic ethers, e.g. dioxan or tetrahydrofuran; acyclic ethers e.g. diethyl ether; amides, e.g. dimethylformamide; esters, e.g. ethyl acetate, and nitriles e.g. acetonitrile.

It will be appreciated that the choice of reducing agent and reaction conditions will be dependent on the nature of the group W.

Suitable reducing agents which may be used in the above process for the reduction of compounds of formula (VIII) wherein W represents, for example, the group —CH(OH)CH$_2$N(CH$_3$)$_2$ include hydrogen in the presence of a metal catalyst, for example Raney Nickel or a noble metal catalyst such as platinum, platinum oxide, palladium or rhodium, which may be supported, for example, on charcoal, kieselguhr or alumina. In the case of Raney Nickel, hydrazine may also be used as the source of hydrogen. This process may conveniently be carried out in a solvent such as an alcohol e.g. ethanol, an ether, e.g. dioxan or tetrahydrofuran, an amide, e.g. dimethylformamide or an ester e.g. ethyl acetate, and at a temperature of from $-10°$ to $+50°$ C., preferably $-5°$ to $+30°$ C.

The reduction process may also be effected on compounds of formula (VIII) wherein W represents, for example, the group —CH(OH)CH$_2$N(CH$_3$)$_2$ or —COCH$_2$N(CH$_3$)$_2$ using an alkali metal or alkaline earth metal borohydride or cyanoborohydride e.g. sodium or calcium borohydride or cyanoborohydride which process may conveniently be carried out in an alcohol such as propanol, ethanol or methanol, and at a temperature of from 10° to 100° C., preferably 50° to 100° C. In some instances, the reduction using a borohydride may be carried out in the presence of cobaltous chloride.

Reductive methylation of the aminoethyl or methylaminoethyl compound corresponding to formula (I) with formaldehyde may be also effected using an alkali metal or alkaline earth metal borohydride or cyanoborohydride. The reaction may be effected in an aqueous or non-aqueous reaction medium, conveniently in an alcohol as just described, or an ether, e.g. dioxan or tetrahydrofuran, optionally in the presence of water. In this embodiment, the reaction may be effected in the presence of an acid e.g. acetic acid, and at a temperature in the range 0° to 100° C., preferably 5° to 50° C.

Reduction of compounds of formula (VIII) wherein W represents, for example, the groups —(CH$_2$)$_2$N(CH$_3$)CHO, —CH$_2$CON(CH$_3$)$_2$, —CH(OH)CH$_2$N(CH$_3$)$_2$, —COCON(CH$_3$)$_2$ and —COCH₂N(CH₃)₂ may also be carried out using a metal hydride such as lithium aluminium hydride. This process may be carried out in a solvent, for example, an ether such as tetrahydrofuran, and conveniently at a temperature of from −10° to +100° C., preferably 50° to 100° C.

A particular embodiment of general process (C) involves the reduction of a compound of formula (VIII) wherein W is the group —CH₂CN, for example, by catalytic reduction with hydrogen in the presence of a catalyst such as palladium on charcoal or rhodium on alumina in the presence of dimethylamine. The reduction may be effected in a suitable solvent such as an alcohol, e.g. methanol or ethanol.

The starting materials or intermediate compounds of general formula (VIII) may be prepared by analogous methods to those described in UK Published Patent Application No. 2124210, or by modification of the 5-position substituent as in process (D) below.

According to another general process (D), the compound of formula (I) may be prepared by reacting a compound of formula (IX)

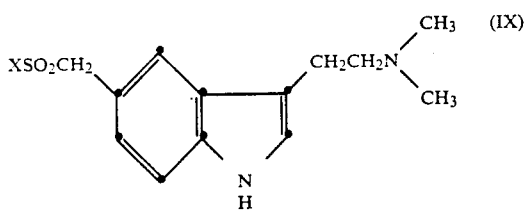

(where X represents a leaving atom or group) or a salt thereof, with methylamine.

Examples of suitable leaving atoms or groups X in the compounds of general formula (IX) include a halogen atom (e.g. a fluorine, chlorine or bromine atom) or a group OR₁₁ where R₁₁ represents a hydrocarbyl group such as an aryl group, e.g. phenyl. The aryl group may be unsubstituted or substituted by one or more substituents such as halogen atoms; or nitro; cyano; amino; alkyl e.g. methyl; alkoxy e.g. methoxy; acyl, e.g. acetyl and alkoxycarbonyl e.g. ethoxycarbonyl groups. The leaving atom or group represented by X is preferably a phenoxy group.

The reaction is conveniently carried out in the presence of a solvent and may be effected in an aqueous or non-aqueous reaction medium.

The reaction medium may thus comprise one or more organic solvents, such as ethers, e.g. dioxan or tetrahydrofuran; amides e.g. N,N-dimethylformamide or N-methylpyrrolidone; alcohols e.g. methanol or ethanol; esters e.g. ethyl acetate; nitriles e.g. acetonitrile; halogenated hydrocarbons e.g. dichloromethane; and tertiary amines e.g. triethylamine or pyridine, optionally in the presence of water. In some cases methylamine may itself serve as the solvent.

If desired the aminolysis may be effected in the presence of a base, such as an alkali metal carbonate or bicarbonate (e.g. sodium or potassium carbonate or bicarbonate); a tertiary amine (e.g. triethylamine or pyridine); an alkoxide (e.g. sodium t-butoxide) or a hydride (e.g. sodium hydride).

The reaction may conveniently be effected at a temperature of from −20° to +150° C.

The starting materials of general formula (IX) wherein X represents a group OR₁₁ may be prepared for example by reduction of a compound of general formula (X)

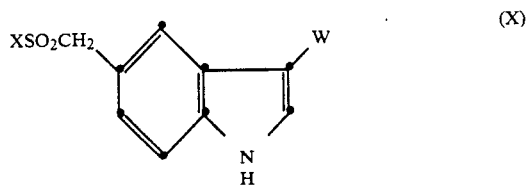

(wherein X is as previously defined and W is the group CH₂CN or CH₂CHO) or a salt or protected derivative thereof, in the presence of dimethylamine, using the general methods described above for general process (C).

A compound of formula (IX) wherein X represents a halogen atom may be prepared for example by reacting the corresponding sulphonic acid derivative or a salt thereof with a halogenating agent such as a phosphorus halide or oxyhalide in an inert organic solvent e.g. phosphorus pentachloride in dichloromethane. A sulphonic acid of formula (IX) where X is OH, may be prepared for example by acid or base catalysed hydrolysis of an ester of formula (IX), (i.e. a compound wherein X represents the group OR₁₁).

Compounds of formula (X) and sulphonic acid derivatives of formula (IX) (wherein X is a hydroxy group) may be prepared by analogous methods to those described in European Published Patent Application No. 145459 and 'A Chemistry of Heterocyclic Compounds—Indoles Part II' Chapter VI edited by W. J. Hamilton (1972) Wiley Interscience, New York.

According to a further general process (E) the compound of formula (I) may be prepared by reacting the compound of formula (XI)

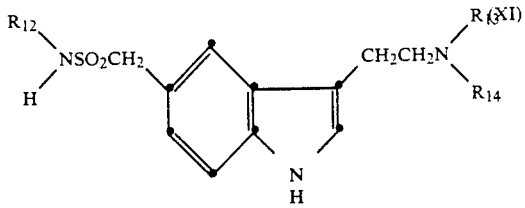

(wherein R₁₂, R₁₃ and R₁₄ each represents hydrogen or a methyl group, at least one of R₁₂, R₁₃ and R₁₄ being hydrogen) with a methylating agent. Methylating agents which may be used in this process include methyl halides (e.g. methyl iodide), methyl tosylate, or dimethylsulphate. It will be appreciated the methylating agent should be used in sufficient quantity to introduce the required number of methyl groups. Thus for example when two of R₁₂, R₁₃ and R₁₄ represent hydrogen at least two equivalents of the methylating agent should be employed. The reaction is conveniently carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides, such as sodium or potassium hydride; alkali metal amides, such as sodium amide; alkali metal carbonates, such as sodium carbonate; or alkali metal alkoxides such as sodium or potassium methoxide, ethoxide or t-butoxide; or tetrabutylammonium fluoride. When a methyl halide is employed as the methylating agent, the reaction may also be carried out in the presence of an acid scavenger such as propylene or ethylene oxide. The reaction may conveniently be effected at temperatures of from 0° to 60° C., preferably 20° to 40° C.

The compound of formula (XI) may be prepared by any of the processes (A)-(E) described herein, or as described in UK Published Patent Application No. 2124210A.

According to a further general process (F), the compound of formula (I) may be prepared by dealkylation of a quaternary ammonium salt of formula (XII):

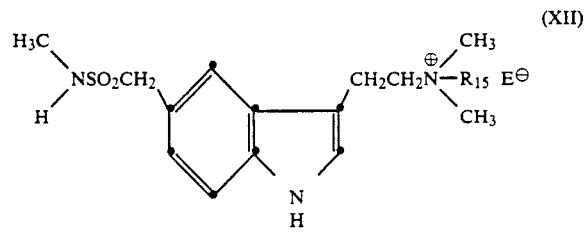

(wherein $R_{15}$ represents a methyl group or $-CH_2CH_2R_{16}$ where $R_{16}$ is an electron-withdrawing group, and $E^{\ominus}$ is an anion e.g. a halide ion).

Electron-withdrawing groups $R_{16}$ include $-SO_3R^a$, $-CO_2^a$, $COR^a$, CHO and CN, where $R^a$ is a hydrocarbyl group, e.g. an alkyl, aryl or aralkyl group. $R_{16}$ is preferably a phenoxysulphonyl group.

Where $R_{15}$ represents a methyl group the dealkylation may be effected by heating the compound (XII) in aqueous ethanolamine, at a temperature in the range 50° to 200° C. A group $-CH_2CH_2R_{16}$ may be removed by treatment with a base such as an alkali metal carbonate, e.g. sodium carbonate or an alkali metal hydroxide e.g. sodium hydroxide.

Compounds of formula (XII) where $R_{15}$ represents a methyl group may be prepared by alkylating the 3-aminoethyl or 3-methylaminoethyl compound corresponding to compound (I), for example as described for general process (E).

Compounds of formula (XII) in which $R_{15}$ represents the group $-CH_2CH_2R_{16}$ may be prepared by reacting the corresponding 3-aminoethyl or 3-methylaminoethyl compound with a compound of formula (XIII):

$$H_2C=CHR_{16} \qquad (XIII)$$

where $R_{16}$ is as previously defined, followed by alkylation of the product as previously described. Reaction with the compound of formula (XIII) may be effected for example in an aqueous medium and at a temperature in the range 0°-50° C.

The compound of formula (I) may also be prepared according to a further general process (G), which comprises dehydrogenation of the corresponding indoline of formula (XIV):

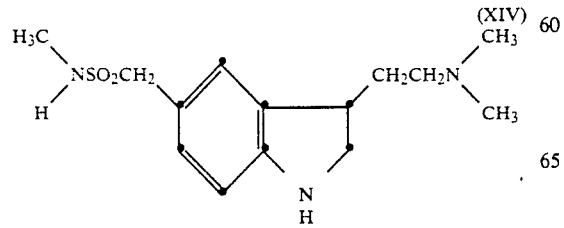

The dehydrogenation process may be carried out in conventional manner either catalytically or using a suitable oxidising agent.

Oxidising agents which may be used in this process include quinones, e.g. 2,3-dichloro-5,6-dicyano-1,4-benzoquinone or 2,3,5,6-tetrachloro-1,4-benzoquinone; and manganese dioxide. Catalytic dehydrogenation of the indoline (XIV) may be effected using for example a palladium, platinum or nickel catalyst, such as palladium on charcoal, finely divided palladium, platinum oxide or Raney nickel.

When an oxidising agent is employed the dehydrogenation reaction may be effected in an aqueous or non-aqueous reaction medium. Solvents which may be used include hydrocarbons e.g. benzene or xylene; amides e.g. N,N-dimethylformamide; ethers e.g. tetrahydrofuran or dioxan; alcohols e.g. methanol or ethanol; halogenated hydrocarbons e.g. dichloromethane; and water, or mixtures thereof. The reaction may be effected at temperatures in the range $-50°$ to $+150°$ C. Catalytic dehydrogenation may be effected in the presence or absence of a solvent, and generally at high temperatures, for example in the range 100° to 300° C. Solvents which may be used thus include inert high-boiling solvents, such as high-boiling hydrocarbons e.g. xylene or isopropyltoluene; and high-boiling ethers, e.g. phenylether. It will be appreciated that the precise reaction conditions will depend upon the oxidising agent or dehydrogenation catalyst used.

The indoline of formula (XIV) may be prepared for example by reduction of the corresponding oxindole, using for example lithium aluminium hydride in a solvent such as an ether e.g. diethyl ether or tetrahydrofuran. The oxindole may be prepared from a compound of formula (XV):

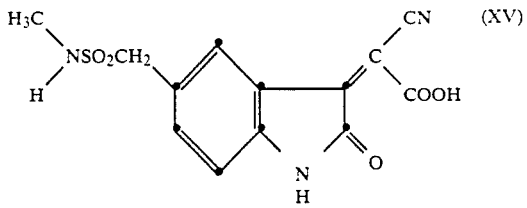

by reduction, for example with hydrogen in the presence of a metal catalyst such as palladium on charcoal, and decarboxylation, e.g. in the presence of quinoline, to give the corresponding 3-cyanomethyl oxindole, followed by reduction in the presence of dimethylamine as described previously for general process (C). The compound of formula (XV) may itself be prepared in conventional manner for example by reacting the aniline of formula (XVI):

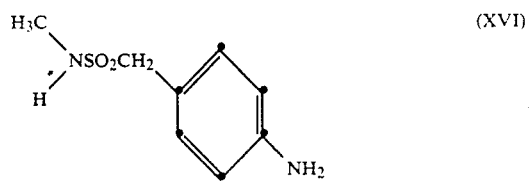

with chloral and hydroxylamine to give an oximinoanilide, cyclising this by treatment with sulphuric acid, and condensing the resulting isatin with cyanoacetic acid in the presence of a base such as triethylamine and in a suitable solvent e.g. dioxan.

According to another general process (H) the compound of formula (I) according to the invention, or a salt thereof, may be prepared by subjecting a protected derivative of the compound of general formula (I) or a salt thereof to a reaction to remove the protecting group or groups.

Thus at an earlier stage in the reaction sequence for the preparation of a compound of general for (I) or a salt thereof it may have been necessary or desirable to protect any sensitive groups in the molecule to avoid undesirable side reactions. For example, it may be necessary to protect the indole nitrogen with, for example, an aralkyl group such as benzyl.

Subsequent cleavage of the protecting group may be achieved by conventional procedures. Thus an aralkyl group such as benzyl, may be cleaved by hydrogenolysis in the presence of a catalyst (e.g. palladium on charcoal) or sodium and liquid ammonia.

As will be appreciated, in some of the general processes (A) to (G) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (G).

Thus, according to a further aspect of the invention, the following reactions in any appropriate sequence, may if necessary and/or desired be carried out subsequent to the processes (A) to (G):

(i) removal of any protecting groups; and
(ii) conversion of the compound of formula (I) or a salt thereof into a physiologically acceptable salt or solvate (e.g. hydrate) thereof.

Where it is desired to isolate the compound of formula (I) as a physiologically acceptable salt, for example as an acid addition salt, this may be achieved by treating the free base of formula (I) with an appropriate acid (e.g. succinic or hydrochloric acid) preferably with an equivalent amount in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. Thus, for example, the methylaminosulphonylmethyl group at the 5-position may be formed either before or after cyclisation to give the indole nucleus. It should therefore be appreciated that in such multi-stage processes, the sequences of reactions should be chosen in order that the reaction conditions do not affect groups present in the molecule which are desired in the final product.

The following examples illustrate pharmaceutical formulations according to the invention, containing 3-[2-(dimethylamino)ethyl]-N-methyl-1H-indole-5-methanesulphonamide succinate (1:1) as the active ingredient. In these examples the weight of the active ingredient is the weight of the succinate.

TABLETS FOR ORAL ADMINISTRATION

A. Direct Compression

| 1. | mg/tablet | for 40 g mix |
|---|---|---|
| Active ingredient | 49 | 15.08 g |
| Magnesium Stearate BP | 0.65 | 0.20 g |

| 1. | mg/tablet | for 40 g mix |
|---|---|---|
| Anhydrous Lactose | 81 | 24.92 g |

The active ingredient was sieved and blended with the anhydrous lactose and magnesium stearate. The resultant mix was compressed into tablets using a Manesty F3 tablet machine fitted with 8.0 mm concave punches.

| 2. | mg/tablet | for 40 g mix |
|---|---|---|
| Active ingredient | 49 | 14.0 g |
| Magnesium Stearate BP | 0.7 | 0.20 g |
| Microcrystalline Cellulose NF | 91 | 26.0 g |

The active ingredient was sieved and blended with the microcrystalline cellulose and magnesium stearate. The resultant mix was compressed into tablets using a Manesty F3 tablet machine fitted with 8.0 mm concave punches.

B. Wet Granulation

| | mg/tablet |
|---|---|
| Active ingredient | 7.0 |
| Lactose BP | 146.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using suitable diameter punches.

Tablets of other strengths may be prepared by altering the ratio of active ingredient to lactose or the compression weight and using punches to suit.

The tablets may be film coated with suitable film-forming materials, such as hydroxypropyl methylcellulose, using standard techniques. Alternatively the tablets may be sugar coated, or enteric coated.

CAPSULES

| | mg/capsule |
|---|---|
| Active ingredient | 49.00 |
| *Starch 1500 | 150.00 |
| Magnesium Stearate BP | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

SYRUP

| Sucrose Free Presentation | mg/5 ml dose |
|---|---|
| Active Ingredient | 49.00 |

-continued

| Sucrose Free Presentation | mg/5 ml dose |
|---|---|
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

SUSPENSION

| | mg/5 ml dose |
|---|---|
| Active ingredient | 49.00 |
| Aluminium monostearate | 75.00 |
| Sweetening agent | |
| Flavour | as required |
| Colour | |
| Fractionated coconut oil to | 5.00 ml |

The aluminium monostearate is dispersed in about 90% of the fractionated coconut oil. The resulting suspension is heated to 115° C. while stirring and then cooled. The sweetening agent, flavour and colour are added and the active ingredient is suitably dispersed. The suspension is made up to volume with the remaining fractionated coconut oil and mixed.

SUB-LINGUAL TABLET

| | mg/tablet |
|---|---|
| Active Ingredient | 49.00 |
| Compressible Sugar NF | 50.5 |
| Magnesium Stearate BP | 0.5 |
| Compression Weight | 100.0 |

The active ingredient is sieved through a suitable sieve, blended with the excipients and compressed using suitable punches. Tablets of other strengths may be prepared by altering either the ratio of active ingredient to excipients or the compression weight and using punches to suit.

SUPPOSITORY FOR RECTAL ADMINISTRATION

| Active ingredient | | 49.0 mg |
|---|---|---|
| *Witepsol H15 | to | 1.0 g |

*A proprietary grade of Adeps Solidus Ph. Eur.

A suspension of the active ingredient in molten Witepsol is prepared and filled, using suitable machinery, into 1 g size suppository moulds.

INJECTION FOR INTRAVENOUS ADMINISTRATION

| | mg/ml |
|---|---|
| Active Ingredient | 0.896 |
| Sodium Chloride Intravenous Infusion, BP, 0.9% w/v | to 1 ml |
| Batch Size | 2500 ml |

The active ingredient was dissolved in a portion of the Sodium Chloride Intravenous Infusion, the solution made to volume with the Sodium Chloride Intravenous Infusion, and the solution thoroughly mixed. The solution was filled into clear, Type 1, glass 10 ml ampoules and sealed under a nitrogen headspace by fusion of the glass. The ampoules were sterilised by autoclaving at 121° C. for not less than 15 minutes.

FOR INHALATION

Inhalation Cartridges

| | mg/cartridge |
|---|---|
| Active ingredient (micronised) | 0.56 |
| Lactose BP | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

Metered Dose Pressurised Aerosol

| Suspension Aerosol | mg/metered dose | Per can |
|---|---|---|
| Active ingredient (micronised) | 0.280 | 73.92 mg |
| Oleic Acid BP | 0.020 | 5.28 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichloromethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

| Nasal Spray | % w/v |
|---|---|
| Active Ingredient | 7.0 |
| Preservative | as required |
| Sodium Chloride BP | |
| Purified Water BP to | 100 |
| Shot Weight | 100 mg (equivalent to 7 mg active ingredient) |

The active ingredient, preservative and sodium chloride are dissolved in a portion of the water, the solution made to volume with the water and the solution thoroughly mixed.

The pH may be adjusted, using acid or alkali, to that of optimum stability and/or to facilitate solution of the active ingredient. Alternatively, suitable buffer salts may be used.

The invention is further illustrated by the following examples. All temperatures are in °C. 'Hyflo' is a filtration aid. "Reactivials" are 4 ml stout-walled glass vials with a screw cap and teflon-faced disc, supplied by Pierce and Warriner (UK) Ltd. Chromatography was carried out either in the conventional manner using silica gel (Merck, Kieselgel 60, Art. 7734) or by 'flash' chromatography (W. C. Still, M. Kahn and A. Mitra, *J. Org. Chem.*, 2923, 43, 1978) on silica (Merck 9385) and thin layer chromatography (t.l.c.) on silica (Macherly-Nagel, Polygram) except where otherwise stated. The following abbreviations define the eluent used for chromatography and t.l.c.:

(A) Ethyl acetate-isopropanol-water-0.88 ammonia 25:15:8:1
(B) Methylene chloride-ethanol-0.88 ammonia 100:8:1
(C) Ether
(D) Methylene chloride-ethanol-0.88 ammonia 20:8:1
(E) Methylene chloride-ethanol-0.88 ammonia 200:8:1
(F) Methylene chloride-ethanol-0.88 ammonia 50:8:1
(G) Ethanol-ethyl acetate-0.88 ammonia-water 25:15:2:2
(H) Isopropanol-chloroform-water-0.88 ammonia 25:15:2:2
(I) Methylene chloride-ethanol-0.88 ammonia 89:10:1
(J) Methylene chloride-methanol 97:3
(K) Ethyl acetate-hexane 60:40
(L) Methylene chloride-methanol 95:5
(M) Ether-hexane 4:1
(N) Methylene chloride-ethanol-0.88 ammonia 25:8:1
(O) Acetic acid-ethyl acetate 1:99
(P) Methylene chloride-ethanol-0.88 ammonia 150:8:1

Intermediates were routinely checked for purity by t.l.c. employing u.v. light for detection and spray reagents such as potassium permanganate (KMnO$_4$). In addition indolic intermediates were detected by spraying with aqueous ceric sulphate (Ce$^{IV}$) and tryptamines by spraying with a solution of iodoplatinic acid (IPA) or ceric sulphate. Proton ($^1$H) nuclear magnetic resonance (n.m.r.) spectra were obtained either at 90 MHz using a Varian EM390 instrument or at 250 MHz using a Bruker AM or WM 250 instrument. s=singlet, d=doublet, t=triplet, q=quartet and m=multiplet.

Preparation 1

(i)
N-Methyl-4-[2-[2-(phenylthio)ethylidene]hydrazino]-benzenemethanesulphonamide A solution of (phenylthio)acetaldehyde (6.05 g) in absolute ethanol (180 ml) was added over 10 min to a solution of 4-hydrazino-N-methylbenzenemethanesulphonamide hydrochloride (10 g) in water (180 ml) with cooling. After addition of the aldehyde was complete, the mixture was stirred at 5° for a period of 14 h. The precipitated solid was filtered off, washed with water (200 ml), hexane (200 ml) and dried in vacuo to give the title compound (10.95 g), m.p. 110°–112°. T.l.c. (B) Rf 0.5 (KMnO$_4$)

(ii)
N-Methyl-3-(phenylthio)-1H-indole-5-methanesulphonamide

A solution of the product of stage (i) (5 g) in absolute ethanol (300 ml) was saturated with hydrogen chloride gas (ca. 30 min) whilst being cooled in an ice-water bath, allowed to stir at ambient temperature for a period of 3 h and then filtered. The filtrate was concentrated in vacuo and chromatographed (flash, E) to afford a foam, which solidified on trituration with ether to an amorphous powder (2.17 g). A sample was recrystallized from hexane-dichloromethane to give the title compound, m.p. 133°–134°. T.l.c. (B) Rf 0.5 (KMnO$_4$)

(iii) N-Methyl-1H-indole-5-methanesulphonamide

To a solution of the product of stage (ii) (460 mg) in absolute ethanol (50 ml) was added Raney Nickel [4.6 g, 50% slurry in water, washed to neutrality with deionized water (60 ml)] and the reaction mixture refluxed for a total of 16 h under an atmosphere of nitrogen. On cooling to ambient temperature, the supernatant was removed and the Raney Nickel extracted with ethanol (2×50 ml, which was brought to a gentle reflux for 15 min under an atmosphere of N$_2$). The combined extracts were filtered through a sand-celite pad and concentrated in vacuo. Chromatography of the residue (flash, E), afforded an oil (187 mg) which crystallised from ether-hexane to give the title compound (90 mg), m.p. 127°–129°. T.l.c. (B) Rf 0.50 (KMnO$_4$)

Preparation 2

5-[[(Methylamino)sulphonyl]methyl]-1H-indole-3-acetic acid 3-(Cyanomethyl)-N-methyl-1H-indole-5-methanesulphonamide (1.0 g) was heated under reflux with stirring under nitrogen with potassium hydroxide (4.5 g) in water (15 ml) and ethanol (25 ml) for 16 h. The ethanol was evaporated at reduced pressure, and the aqueous residue diluted with water (20 ml) and washed with ethyl acetate (2×30 ml). The aqueous layers were acidified with 2N hydrochloric acid (50 ml) and extracted with ethyl acetate (3×50 ml); the latter organic layers were washed with brine, dried (MgSO$_4$) and evaporated to give an oil (1.25 g). Trituration with dry ether gave the title compound as a solid (0.767 g) m.p. 126°–133°. T.l.c. (O), Rf 0.7 (CeIV)

Preparation 3

3-[2-(Dimethylamino)ethyl]-2,3-dihydro-N-methyl-1H-indole-5-methanesulphonamide

To a suspension of 3-[2-(dimethylamino)ethyl]-N-methyl-1H-indole-5-methanesulphonamide (0.5 g) in trifluoroacetic acid (15 ml) at −10° was added borane-tetrahydrofuran complex (45 ml; 1M) keeping the temperature below +2°. The resulting suspension was stirred at 0° for 5 min, poured onto saturated potassium carbonate (50 ml) and extracted with ethanol (2×20 ml). The ethanolic extract was evaporated and the residue purified by column chromatography (A) to give the title compound as an oil (80 mg). T.l.c. (N), Rf 0.53 (IPA, Ce$^{IV}$).

Unless otherwise indicated the following examples illustrate the preparation of 3-[2-(dimethylamino)ethyl]-N-methyl-1H-indole-5-methane sulphonamide and salts thereof.

EXAMPLE 1

Compound with succinic acid (2:1) (hemisuccinate)

A solution of 3-(cyanomethyl)-N-methyl-1H-indole-5-methanesulphonamide (16.5 g) in methanolic dimethylamine (200 ml, 15% w/w) and ethanolic dimethylamine (300 ml, 33% w/w) was hydrogenated at room temperature over pre-reduced palladium oxide on charcoal (10%, 16 g) in ethanol (100 ml) for 24 h. The suspension was filtered through hyflo and evaporated in vacuo to give a solid (16 g) which was triturated with diethyl ether (500 ml). The solid (13.5 g) was collected by filtration and dissolved in hot absolute ethanol (200 ml) and filtered. To the hot filtrate was added a solution of succinic acid (2.7 g) in methanol (50 ml). The crystals that formed were removed by filtration to give the title compound (12.2 g) m.p. 158°–159°. T.l.c. (D) Rf 0.5 (IPA)

Analysis Found: C,54.0; H,6.7; N,11.7. $(C_{14}H_{21}N_3O_2S)_2.C_4H_6O_4$ requires C,54.2; H,6.8; N,11.9%.

$^1$H n.m.r. $\delta(DMSO-d_6)$, 2.37(2H,s,$CH_2CO_2H$), 2.40[6H,s,N($CH_3)_2$], 2.58(3H,s,NH$CH_3$) 2.7–3.0(4H,m,$CH_2CH_2N$), 4.38(2H,s,$CH_2SO_2$), 6.85(1H,brs, NH$CH_3$), and aromatic signals at 7.11(1H,brd), 7.22(1H,brs), 7.36(1H,d), 7.55(1H,brs) and 10.94(1H,brs)

EXAMPLE 2

Compound with succinic acid (1:1)

A solution of 3-(2-aminoethyl)-N-methyl-1H-indole-5-methanesulphonamide (2 g) and sodium cyanoborohydride (0.564 g) in methanol (37.5 ml) and acetic acid (2.246 g) was treated at ca. 12° with a solution of 36% w/v aqueous formaldehyde (1.25 ml) in methanol (8.85 ml). The resulting solution was stirred at 22° for 2 h, followed by the addition of 2N sodium hydroxide solution (6.5 ml) and sodium borohydride (0.1 g). 2N hydrochloric acid (7 ml) was added to the reaction mixture which was then evaporated free of methanol, and diluted with water (to 25 ml). Solid potassium carbonate was added to pH 7, the solution was washed with ethyl acetate and the ethyl acetate extracts were washed with water. The aqueous layer and washings were combined, saturated with potassium carbonate and extracted with ethyl acetate. The ethyl acetate extracts were dried (MgSO$_4$) and evaporated to a solid residue (1.8 g). 1.67 g of the residue was recrystallised from isopropanol (16.7 ml) to give 1.307 g, of crystalline base, 1.297 g of which was dissolved in IMS (13 ml) and treated with a hot solution of succinic acid (0.518 g) in IMS (13 ml). The resulting solution was cooled and the precipitated solid filtered and dried to give title compound (1.737 g) m.p. 165°–166°. The n.m.r. and t.l.c. [(G), Rf 0.5 (IPA)] were in agreement with the product of Example 1.

EXAMPLE 3

3-[2-(Dimethylamino)ethyl]-N-methyl-1H-indole-5-methanesulphonamide (Base)

Solutions of sodium borohydride (7.1 g) in water (100 ml) and formalin (36% w/v, 50 ml) in methanol (50 ml) were added to a solution of 3-(2-aminoethyl)-N-methyl-1H-indole-5-methanesulphonamide (10 g) in methanol (200 ml) at 15°–21° during 0.75 h. Hydrochloric acid (2N, 75 ml) was added and the mixture concentrated in vacuo to 150 ml. Further hydrochloric acid (2N, 50 ml) was added. The mixture was basified with potassium carbonate (60 g) and extracted with ethyl acetate (2×150 ml). The combined extracts were dried (MgSO$_4$) and concentrated in vacuo to give the title compound (10.7 g) as a solid m.p. 169°–171°. T.l.c. (G), Rf 0.5 (u.v.) and n.m.r. spectrum were in agreement with the product of Example 1.

EXAMPLE 4

(i)

N,N-Dimethyl-5-[2-[(methylamino)sulphonyl]methyl]-α-oxo-1H-indole-3-acetamide

Oxalyl chloride (0.112 ml) was added to a stirred solution of N-methyl-1H-indole-5-methanesulphonamide (270 mg) contaminated with phthalimide (ca. 40% w/w) in dry tetrahydrofuran under nitrogen, and stirring was continued at room temperature for 1.75 h. Gaseous dimethylamine was bubbled through the reaction mixture for 15 min, and stirring was continued at room temperature for a further 15 min. The mixture was poured into 2N hydrochloric acid (50 ml) and extracted with ethyl acetate (3×20 ml); the organic layers were washed with brine, dried (MgSO$_4$) and evaporated to give a foam (222 mg). Purification by flash chromatography (J) gave the title compound as a solid (126 mg) m.p. 157°–159°. T.l.c. (L) Rf 0.15 (u.v.)

(ii)

3-[2-(Dimethylamino)ethyl]-N-methyl-1H-indole-5-methanesulphonamide

The product of Stage (i) (77 mg) was heated under reflux with lithium aluminium hydride (90 mg) in dry tetrahydrofuran (15 ml) with stirring under nitrogen for 4 h. After cooling to room temperature, water (0.09 ml) was cautiously added under nitrogen, followed by 2N aqueous sodium hydroxide (0.18 ml) and more water (0.18 ml). The precipitate was filtered off, and the filtrate evaporated to give an oil (53 mg) which was shown by its n.m.r. spectrum and t.l.c. to be identical with the product of Example 1.

EXAMPLE 5

(i)

3-(Chloroacetyl)-N-methyl-1H-indole-5-methanesulphonamide

To N,N-diethyl chloroacetamide (800 mg) at 0° was added phosphorous oxychloride (250 μl) over a period of 30 sec. After the addition was complete, the mixture was allowed to stir at 0° for 15 min and then at room temperature for 20 min. The product of Preparation 1 (300 mg) was added at 0° and the mixture warmed to 65°, whereupon it dissolved. The mixture was stirred for 2 h at this temperature then poured onto ice (ca. 5 g) and chloroform (5 ml) and stirred vigorously for 1 h. A solid was filtered off, washed with water (50 ml), and hexane (100 ml) and dried in vacuo to give the title compound (192 mg)

T.l.c. (B) Rf 0.42 (KMnO$_4$)

$^1$H n.m.r. $\delta(DMSO-d_6)$, 2.58(3H,d,NH$CH_3$), 4.45(2H,s,$CH_2SO_2$), 4.92(2H,s,$CH_2Cl$), 6.88(1H,q,NH) and aromatic signals at 7.29(1H,dd), 7.54(1H,d), 8.23(1H,brs), 8.50(1H,d) and 12.30(1H,brs,indole NH)

(ii)

3-[(Dimethylamino)acetyl]-N-methyl-1H-indole-5-methanesulphonamide

A solution of the product of stage (i) (160 mg) in ethanolic dimethylamine (30 ml, 33% w/v solution in ethanol) was heated to reflux for a period of 2 h. On cooling to ambient temperature the solvent was removed in vacuo and the residue was chromatographed (B) to afford the title compound (55 mg) m.p. 230° (decomp.) T.l.c. (B) Rf 0.14 (IPA)

(iii)
3-[2-(Dimethylamino)ethyl]-N-methyl-1H-indole-5-methanesulphonamide To a suspension of the product of stage (ii) (46.5 mg) in 1-propanol (5 ml) was added sodium borohydride (62 mg). The reaction mixture was brought to reflux for a period of 3 h, then an additional quantity of borohydride (60 mg) was added. After refluxing for a further 1 h, the mixture was allowed to cool to ambient temperature and quenched with 2N HCl (10 ml). The aqueous solution was washed with ethyl acetate (5 ml) then neutralized (satd. NaHCO$_3$ solution) and extracted with ethyl acetate (3×15 ml). The combined extracts were dried (MgSO$_4$) and concentrated in vacuo and the residue chromatographed (F) to give the title compound as a gum (2 mg) which was shown by t.l.c. [(F), Rf 0.34, (KMnO$_4$)] and n.m.r. to be identical with the product of Example 1.

EXAMPLE 6

(i)
N,N-Dimethyl-5-[[(methylamino)sulphonyl]methyl]-1H-indole-3-acetamide To a solution of the product of Preparation 2 (0.3 g) in tetrahydrofuran (20 ml) was added 1,1'-carbonyldiimidazole (0.24 g) and stirred at room temperature for 1 h. It was then treated with tetrahydrofuran (20 ml) saturated with dimethylamine and then left at ambient temperature for 16 h. The resulting suspension was treated with concentrated ammonium hydroxide (d 0.88; 1 ml), the solvent evaporated and the residue purified by column chromatography (B). The title compound was obtained as an amorphous solid (0.18 g)

T.l.c. (B) Rf 0.4 (Ce$^{IV}$).

$^1$H n.m.r. δ(DMSO-d$_6$), 2.56(3H,d,NHMe), 2.84 & 3.04(6H,s+s, CONMe$_2$), 3.74(2H,s,CH$_2$CO), 4.33(2H,s,CH$_2$SO$_2$), 6.81(1H,q,NHMe), and aromatic signals at 7.11(1H,dd), 7.23(1H,d), 7.35(1H,d), 7.57(1H,brs) and 11.00(1H,brs, indole NH)

(ii)
3-[2-(Dimethylamino)ethyl]-N-methyl-1H-indole-5-methanesulphonamide To a mixture of lithium aluminium hydride (0.2 g) in dry tetrahydrofuran (10 ml) was added the product of stage (i) (0.17 g) and the resulting mixture heated at reflux for 16 h. The excess of lithium aluminium hydride was destroyed by water (2 ml), the reaction mixture partitioned between saturated potassium carbonate (10 ml) and ethanol (10 ml), and the ethanol layer evaporated to dryness. The residue was purified by column chromatography (F) to give the title compound as an oil (0.12 g) which was shown by n.m.r. and t.l.c. to be identical with the product of Example 1.

EXAMPLE 7

(i) Phenylmethyl methyl[2-[5-[[(methylamino)sulphonyl]methyl]-1H-indol-3-yl]ethyl]carbamate To a cold (ice bath) solution of N-methyl-3-[(2-methylamino)ethyl]-1H-indole-5-methanesulphonamide (0.55 g) in sodium carbonate (2N; 15 ml) and tetrahydrofuran (10 ml) was added benzylchloroformate (0.3 ml) and the resulting suspension stirred at room temperature overnight. It was then poured onto ice, extracted with dichloromethane (3×30 ml), and the extracts dried (MgSO$_4$) and concentrated. The residue was purified by column chromatography (C) to give the title compound as a foam (0.58 g)

T.l.c. (C) Rf 0.3 (Ce$^{IV}$, KMnO$_4$).

$^1$H n.m.r. δ(DMSO-d$_6$ at 330K), 2.58(3H,s,NHMe) 2.93(3H,s,N-Me), 2.98(2H,m,NCH$_2$CH$_2$), 3.60(2H,m,NCH$_2$CH$_2$), 4.35(2H,s,CH$_2$SO$_2$), 5.12(2H,s,CH$_2$Ph), 6.59(1H,brs,NHCH$_3$), and aromatic signals at 7.1-7.2(2H,m), 7.3-7.5(6H,m), 7.58(1H,brs) and 10.80(1H,brs,indole NH)

(ii)
3-[2-(Dimethylamino)ethyl]-N-methyl-1H-indole-5-methanesulphonamide A mixture of the product of stage (i) (0.2 g) and lithium aluminium hydride (0.3 g) in dry tetrahydrofuran (50 ml) was heated at reflux for 6 h then cooled and the excess of lithium aluminium hydride decomposed by addition of water (5 ml). The resulting suspension was saturated with solid potassium carbonate and extracted with ethanol (2×30 ml). The solvent was evaporated and the residue purified by column chromatography (F) to give an oil (67 mg) which was shown by n.m.r. and t.l.c. [(D), Rf 0.5] to be identical with the product of Example 1.

EXAMPLE 8

Compound with succinic acid (2:1)

(i)
4-[2-[4-(Dimethylamino)butylidene]hydrazino]-N-methylbenzenemethanesulphonamide 4,4-Dimethoxy-N,N-dimethylbutanamine (8.32 g) was added to a stirred suspension of 4-hydrazino-N-methylbenzenemethanesulphonamide hydrochloride (10 g) in water (25 ml) and 2N hydrochloric acid (5 ml). Further 2N hydrochloric acid (15 ml) was added to give a solution (pH 1.5-2) which was stirred for 2.5 h at room temperature. Chloroform (150 ml) was added followed by 2N sodium carbonate solution (150 ml) in 25 ml aliquots. The layers were separated and the aqueous layer was further extracted with chloroform (150 ml). The combined organic extracts were dried (MgSO$_4$) and concentrated in vacuo to give the title compound as a foam (12.4 g). T.l.c. alumina, (E), Rf 0.45.

ii)
3-[2-(Dimethylamino)ethyl]-N-methyl-1H-indole-5-methanesulphonamide, compound with succinic acid (2:1)

A mixture of polyphosphate ester (20 g) and the product of Stage (i) (4 g) in chloroform (80 ml) was stirred at room temperature for 4 h. The reaction mixture was extracted with water (2×100 ml), the aqueous extracts washed with chloroform (50 ml), then basified to pH 11 with solid potassium carbonate and extracted with ethyl acetate (3×100 ml). The combined organic extracts were dried (MgSO$_4$) and concentrated in vacuo to leave a foam (2.5 g), which was chromatographed (F) to give the tryptamine as an oil (1.13 g) which slowly crystallised on standing. Succinic acid (0.22 g) in hot methanol (4 ml) was added to a hot solution of the tryptamine (1.1 g) in absolute ethanol (21 ml) and the mixture was heated to reflux with stirring to give a solution. The solution was allowed to cool with stirring to room temperature, and the resultant suspension was further cooled in an ice-bath for 2 h. The solid was filtered off,

EXAMPLE 9

(i)
3-(2-Hydroxyethyl)-N-methyl-1H-indole-5-methanesulphonamide

A mixture of the product of Preparation 2 (0.5 g) and lithium aluminium hydride (1 g) in dry tetrahydrofuran was heated at reflux for 16 h. The excess of the hydride was destroyed with water (2 ml) and the resulting suspension partitioned between saturated potassium carbonate (10 ml) and ethanol (10 ml). The organic layer was evaporated to dryness and the residue purified by column chromatography (B) to give the title compound as a solid (0.2 g). T.l.c. (P) Rf 0.2 (KMnO$_4$, Ce$^{IV}$) $^1$H n.m.r. δ(DMSO-d$_6$), 2.56(3H,d,NHMe), 2.87(2H,m,CH$_2$CH$_2$OH), 3.67(2H,m,CH$_2$CH$_2$OH), 4.37(2H,s,CH$_2$SO$_2$), 6.81(1H,m,NHMe), and aromatic signals between 7.09 and 10.90.

(ii)
3-[2-(Dimethylamino)ethyl]-N-methyl-1H-indole-5-methanesulphonamide

To a cold solution of the product of stage (i) (70 mg) in pyridine (2 ml) (ice-salt bath) was added a cold solution of thionyl chloride (1 ml) in pyridine (3 ml) (ice-salt bath) and the resulting solution stirred for 0.5 h during which time temperature rose to +10°. It was then quenched with ice, acidified with conc. hydrochloric acid and extracted with dichloromethane (3×20 ml). Evaporation of the solvent gave 3-(2-chloroethyl)-N-methyl-1H-indole-5-methanesulphonamide as an oil (30 mg) which was dissolved in ethanolic dimethylamine (33% w/v, 5 ml) and heated in a reactivial for 4 h at 100°. Evaporation of the solvent gave an oil which was shown by t.l.c. [(F), Rf 0.35] to contain the product of Example 1. In another experiment 3-(2-chloroethyl)-N-methyl-1H-indole-5-methanesulphonamide was obtained pure as an oil after chromatography (B)
$^1$H n.m.r. δ(DMSO-d$_6$), 2.60(3H,d,NHMe), 3.20(2H,m,CH$_2$CH$_2$Cl), 3.90(2H,m,CH$_2$CH$_2$Cl), 4.40(2H,s,CH$_2$SO$_2$), 6.87(1H,brs,NHMe), and aromatic signals between 7.15 and 11.08.

EXAMPLE 10

Methylamine was bubbled through a solution of phenyl 3-[2-(dimethylamino)ethyl]-1H-indole-5-methanesulphonate (0.223 g) in anhydrous pyridine. The solution was then heated in an autoclave at 120° (oil bath temperature) for 16 h. Pyridine was removed by rotary evaporation and the residual gum purified by chromatography (F). Evaporation of the appropriate fractions produced a partially crystalline gum (0.11 g) which solidified on scratching to present a powder (0.1 g) m.p. 169°–172° shown by n.m.r. and t.l.c. [(F), Rf 0.4 (IPA)] to be identical with the product of Example 1.

EXAMPLE 11

A solution of 3-[2-(dimethylamino)ethyl]-1H-indole-5-methanesulphonamide in anhydrous tetrahydrofuran (THF) (5 ml) was treated with tetra-n-butylammonium fluoride (1M in THF, 0.16 ml) and stirred at room temperature for 25 min. Propylene oxide (0.01243 ml) was added, followed by methyl iodide (0.005 ml) and the solution stirred at room temperature. After 3 h, t.l.c. [(N), Rf 0.7] showed the presence of the product of Example 1.

EXAMPLE 12

To a cold (ice bath) solution of N-methyl-3-[2-(methylamino)ethyl]-1H-indole-5-methanesulphonamide (0.3 g) in ethanol (10 ml) was added methyl iodide (0.07 ml) and the resulting solution stirred at ambient temperature overnight. It was then acidified with dilute hydrochloric acid to pH 1, extracted with ethyl acetate (25 ml) and the acidic layer partitioned between saturated potassium carbonate (20 ml) and ethanol (20 ml). The ethanol layer was evaporated and the residue purified by column chromatography (F) to give an oil (30 mg) which was shown by n.m.r. and t.l.c. [(D), Rf 0.5] to be identical with the product of Example 1.

EXAMPLE 13

Iodomethane (0.16 ml) was added to a stirred mixture of 3-(2-aminoethyl)-N-methyl-1Hindole-5-methanesulphonamide (0.2 g) and sodium hydrogen carbonate (0.14 g) in methanol (10 ml). The mixture was stirred at 22° for 2 h and at reflux for 16 h. More iodomethane (0.5 ml) was added and the mixture was stirred at reflux for 2 h longer. The mixture was filtered, and the solvent removed by distillation at reduced pressure to give an oil containing N,N,N-trimethyl-5-[[(methylamino)sulphonyl]methyl]-1H-indole-3-ethanaminium iodide. 50% Aqueous ethanolamine (20 ml) was added and the mixture was heated at reflux for 1 h. The water was distilled off and the resulting solution was heated at 100° for 1 h. Water (25 ml), ethyl acetate (25 ml) and anhydrous potassium carbonate (10 g) were added. The mixture was shaken and allowed to separate to give three phases. The uppermost ethyl acetate layer was collected, washed with water (5 ml), dried (MgSO$_4$) and the solvent removed by distillation at reduced pressure to give the title compound as a gum (0.1 g), shown by t.l.c. [(D) Rf 0.75 (IPA)] to be identical with the product of Example 1.

EXAMPLE 14

To a solution of the product of Preparation 3 (40 mg) in dioxan (20 ml) was added 2,3-dichloro-5,6-dicyano-1,4-benzoquinone (35 mg) and the mixture heated at reflux for 2 h. It was cooled, partitioned between saturated potassium carbonate (20 ml) and ethanol (20 ml), and the organic layer evaporated to an oil (10 mg) which was shown by t.l.c. [(F), Rf 0.31] to contain the product of Example 1.

EXAMPLE 15

(i)
3-(Cyanomethyl)-N-methyl-1-(phenylmethyl)-1H-indole-5-methanesulphonamide 3-(Cyanomethyl)-N-methyl-1H-indole-5-methanesulphonamide (0.4 g) was dissolved in re-distilled dimethylformamide (10 ml) and treated with sodium hydride (0.132 g, 80% dispersion in oil). After 0.5 h the stirred suspension was cooled to −30° C. and treated with distilled benzyl chloride (0.19 g). The mixture was allowed to warm to 10°, stirred for 1 h and then poured onto ice (10 g). The suspension was filtered, and the solid collected and washed with water (20 ml) and cyclohexane (30 ml). The solid was purified by chromatography (M) and the appropriate fractions were comwashed with ethanol (25 ml), and dried in vacuo to give the title compound (0.83 g), m.p. 152°–155° C. which was shown from its n.m.r. spectrum and t.l.c. [(D), Rf 0.5, (IPA)] to be identical with the product of Example 1.

bined and concentrated in vacuo to 20 ml, whereupon a solid crystallised out which was collected and dried to give the title compound (0.12 g), m.p. 133°–135°. T.l.c. (M), Rf 0.4, (KMnO4)

(ii)

3-[2-(Dimethylamino)ethyl]-N-methyl-1-(phenylmethyl)-1H-indole-5-methanesulphonamide A solution of the product of Stage (i) (100 mg) in ethanolic dimethylamine (3 ml, 33% w/w) was hydrogenated over pre-reduced dry 10% palladium oxide on carbon (100 mg) in ethanol (10 ml) for 4 h at 21°. The catalyst was filtered off (hyflo) and the solvent evaporated in vacuo to give a gum (100 mg) which was purified by chromatography (B) to give the title compound (0.85 mg) as a foam. T.l.c. (B) Rf 0.3

(iii)

3-[2-(Dimethylamino)ethyl]-N-methyl-1H-indole-5-methanesulphonamide

To a stirred solution of sodium (ca. 15 mg) in liquid ammonia (3 ml) cooled to −60° was added the product of Stage (ii) (75 mg) in tetrahydrofuran (1 ml) dropwise. After 5 min methanol (0.5 ml) and ammonium chloride (0.2 g) were added and the ammonia was evaporated at 40°. The mixture was concentrated in vacuo to give a solid (0.8 g) which was purified by chromatography (F) to give the title compound (20 mg) as a powder m.p. 160°–165° which was shown by n.m.r. and t.l.c. [(F), Rf 0.4] to be identical with the product of Example 1.

EXAMPLE 16

Compound with fumaric acid (2:1)

A hot solution of the product of Example 3 (590.8 mg) in IMS (7 ml) was treated in a single portion, with a hot solution of fumaric acid (128 mg) in IMS (8.0 ml), and the mixture cooled to 25°. The resulting suspension was stirred with ice-cooling for 30 min and filtered. The filter-cake was washed with IMS (2 ml) and dried in vacuo to give the title compound (619 mg) m.p. 204.5°–206° (dec.).

Analysis Found: C,54.1; H,6.7; N,11.7. $(C_{14}H_{21}N_3O_2S)_2.C_4H_4O_4$ requires C,54.4; H,6.6; N,11.9%.

EXAMPLE 17

Compound with benzoic acid

A hot solution of the product of Example 3 (590.8 mg) in IMS (7 ml) was treated in a single portion with a hot solution of benzoic acid (244 mg) in IMS (2 ml). The solution was allowed to cool to 25°. The resulting suspension was stirred under ice-cooling for 20 min and filtered. The filter cake was washed with IMS (0.5 ml) and dried in vacuo to yield the title compound (653 mg) m.p. 173°–175°

Analysis Found: C,60.3; H,6.6; N,9.9. $C_{14}H_{21}N_3O_2S.C_7H_6O_2$ requires: C,60.4; H,6.5; N,10.1%.

EXAMPLE 18

Compound with methanesulphonic acid (1:1)

A solution of methanesulphonic acid (0.213 g) in hot IMS (3 ml) was added to a stirred solution of the product of Example 3 (0.597 g) in hot IMS (9 ml). The resulting stirred solution was allowed to cool to room temperature over 1 h, cooled in an ice bath for 20 min, and the mixture was then filtered. The title salt was obtained as a solid (0.642 g), m.p. 186°–188.5°.

Analysis Found: C,46.0; H,6.6; N,10.6. $C_{14}H_{21}N_3O_2S.CH_4O_3S$ requires C,46.0; H,6.4; N,10.7% T.l.c. (H) Rf 0.23 (trace impurity), 0.52; (IPA, $Ce^{IV}$)

EXAMPLE 19

Compound with succinic acid (1:1)

A hot clarified solution of succinic acid (1.26 g) in IMS (10 ml) as added to a stirred clarified solution of the product of Example 3 (3.14 g) in IMS (60 ml) at 70°. Solid began to crystallise out almost immediately, and the stirred mixture was allowed to cool to 30°. The stirred mixture was further cooled in an ice-bath (45 min). The solid was filtered off, washed with cold ethanol (35 ml) and dried in vacuo to give the title compound (4.17 g) m.p. 164°–165°. T.l.c. (D) Rf 0.7 (IPA, $Ce^{IV}$).

$^1$H n.m.r. and g.l.c. indicate the product contains 5.52% w/w ethanol (0.52 mol)

Analysis Found: C,51.7; H,6.95; N,9.8. $C_{14}H_{21}N_3O_2S.C_4H_6O_4.0.52C_2H_6O$ requires C,52.25; H,6.95; N,9.6%.

EXAMPLE 20

Compound with hydrogen chloride (1:1)

Concentrated hydrochloric acid (0.18 ml) was added to a stirred solution of the product of Example 3 (504 mg) in IMS (4 ml) at 65°. The mixture was allowed to cool to 25° when a solid crystallised. Ice-cooling was applied and the solid was collected by filtration. The cake was washed with (IMS 2×1 ml) and dried at reduced pressure to give the title compound (517 mg) m.p. 214°–215°. T.l.c. (G), Rf 0.47 (IPA)

Analysis Found: C,50.75; H,6.8; N,12.6. $C_{14}H_{21}N_3O_2S.HCl$ requires C,50.5; H,6.7; N,12.7%.

I claim:

1. A compound of formula (I):

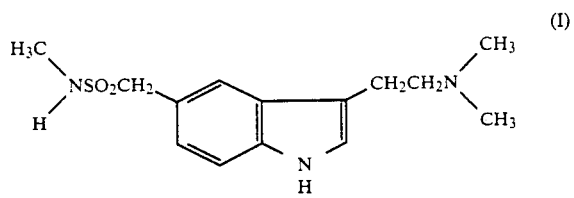

and its physiologically acceptable salts and solvates.

2. A compound according to claim 1, wherein the physiologically acceptable salt is an acid addition salt formed with an organic or inorganic acid.

3. A compound according to claim 2, wherein the physiologically acceptable salt is a hydrochloride, hydrobromide, sulphate, nitrate, phosphate, formate, mesylate, citrate, benzoate, fumarate, maleate or succinate.

4. A compound according to claim 3, wherein the physiologically acceptable salt is the 1:1 succinate.

5. A pharmaceutical composition comprising as active ingredient an effective amount of the compound of formula (I) as defined in claim 1 or a physiologically acceptable salt or solvate thereof, together with one or more pharmaceutically acceptable carriers or excipients for use in the treatment or prevention of pain resulting from dilatation of the cranial vasculature.

6. A pharmaceutical composition according to claim 5 which is formulated for oral administration to humans.

7. A pharmaceutical composition according to claim 6, which is formulated in unit dosage form comprising 0.1 mg to 100 mg of active ingredient.

8. A pharmaceutical composition according to claim 7, which is formulated in unit dosage form comprising 0.5 mg to 50 mg of active ingredient.

9. A pharmaceutical composition according to claim 8, which is formulated in unit dosage form comprising 2 mg to 40 mg of active ingredient.

10. A method of treating a human being susceptible to or suffering from migraine which comprises administering an effective amount of a compound of formula (I) as defined in claim 1 or a physiologically acceptable salt or solvate thereof.

11. A method of treating a human being susceptible to or suffering from migraine which comprises administering a pharmaceutical composition according to claim 5.

12. A method of treating a human being susceptible to or suffering from migraine which comprises administering by the oral route a pharmaceutical composition according to claim 6.

* * * * *